US006381482B1

(12) United States Patent
Jayaraman et al.

(10) Patent No.: US 6,381,482 B1
(45) Date of Patent: *Apr. 30, 2002

(54) FABRIC OR GARMENT WITH INTEGRATED FLEXIBLE INFORMATION INFRASTRUCTURE

(75) Inventors: Sundaresan Jayaraman, Atlanta; Sungmee Park, Tucker; Rangaswamy Rajamanickam; Chandramohan Gopalsamy, both of Atlanta, all of GA (US)

(73) Assignee: Georgia Tech Research Corp., Atlanta, GA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/273,175

(22) Filed: Mar. 19, 1999

Related U.S. Application Data

(60) Provisional application No. 60/085,266, filed on May 13, 1998, now abandoned.

(51) Int. Cl.[7] ................................................. A61B 5/04
(52) U.S. Cl. ........................ 600/388; 600/390; 600/393; 600/395
(58) Field of Search ................................. 600/372, 384, 600/386, 388–390, 395–397; 607/115, 148, 149, 152; 2/2.5; 428/911; 73/54.23, 54.38

(56) References Cited

U.S. PATENT DOCUMENTS

| 2,579,383 A | 12/1951 | Goudsmit |
| 3,020,935 A | 2/1962 | Balis |
| 3,409,007 A | 11/1968 | Fuller |

(List continued on next page.)

OTHER PUBLICATIONS

Slide Presentation Titled High Velocity Penetration Analysis from the DLA/ARPA/NRaD Sensate Liner Workshop held Apr. 11, 1996; Author: Dr. Robert Eisler, MRC., Inc.

Slide Presentation Tilted Introducing Clarity Fit Technologies from the DLA/ARPA/NRaD Sensate LIner Workshop held Apr. 11, 1996; Author: Edith Gazzuolo, Clarity Inc.

(List continued on next page.)

*Primary Examiner*—Linda C. M. Dvorak
*Assistant Examiner*—David M. Ruddy
(74) *Attorney, Agent, or Firm*—Todd Deveau; Jacqueline Haley; Troutman Sanders LLP

(57) ABSTRACT

A fabric, in the form of a woven or knitted fabric or garment, including a flexible information infrastructure integrated within the fabric for collecting, processing, transmitting and receiving information concerning—but not limited to—a wearer of the fabric. The fabric allows a new way to customize information processing devices to "fit" the wearer by selecting and plugging in (or removing) chips/sensors from the fabric thus creating a wearable, mobile information infrastructure that can operate in a stand-alone or networked mode. The fabric can be provided with sensors for monitoring physical aspects of the wearer, for example body vital signs, such as heart rate, EKG, pulse, respiration rate, temperature, voice, and allergic reaction, as well as penetration of the fabric. The fabric consists of a base fabric ("comfort component"), and an information infrastructure component which can consist of a penetration detection component, or an electrical conductive component, or both. The preferred penetration detection component is a sheathed optical fiber. The information infrastructure component can include, in addition to an electrically conductive textile yarn, a sensor or a connector for a sensor. A process is provided for making an electrical interconnection between intersecting electrically conductive yarns. Furthermore, a process is established for sheathing the plastic optical fiber and protecting it.

31 Claims, 14 Drawing Sheets

U.S. PATENT DOCUMENTS

| | | | |
|---|---|---|---|
| 3,610,250 A | * 10/1971 | Sarbacher | 607/149 |
| 4,299,878 A | 11/1981 | Rheaume | |
| 4,572,197 A | 2/1986 | Moore et al. | |
| 4,580,572 A | 4/1986 | Granek et al. | |
| 4,668,545 A | 5/1987 | Lowe | |
| 4,708,149 A | * 11/1987 | Axelgaard et al. | 607/152 |
| 4,722,354 A | * 2/1988 | Axelgaard et al. | 607/152 |
| 4,727,603 A | 3/1988 | Howard | |
| 4,729,377 A | * 3/1988 | Granek et al. | 128/639 |
| 5,103,504 A | 4/1992 | Dordevic | |
| 5,212,379 A | 5/1993 | Nafarrate et al. | |
| 5,316,830 A | 5/1994 | Adams, Jr. et al. | |
| 5,374,283 A | * 12/1994 | Flick | 607/46 |
| 5,415,204 A | 5/1995 | Kitamura | |
| 5,436,444 A | 7/1995 | Raswon | |
| 5,450,845 A | * 9/1995 | Axelgaard | 128/640 |
| 5,624,736 A | 4/1997 | DeAngelis et al. | |
| 5,636,378 A | 6/1997 | Griffith | |
| 5,694,645 A | 12/1997 | Triplette | |
| 5,766,236 A | * 6/1998 | Detty et al. | 607/149 |
| 6,151,528 A | * 11/2000 | Maida | 607/149 |

OTHER PUBLICATIONS

Slide Presentation Titled Silicone Rubber Fiber Optic Sensors from the DLA/ARPA/NRaD Sensate Liner Workshop held Apr. 11, 1996; Author: Jeffrey D. Muhs.

Slide Presentation Titled Vital Sign Sensing from the DLA/ARPA/NRaD Sensate Liner Workshop held Apr. 11, 1996; Author: Dr. Herman Watson, NIMS, Inc.

Slide Presentation Titled Sensate LIner Design & Development: Georgia Tech's Potential Contributions From the DLA/ARPA/NRaD Sensate Liner Workshop held Apr. 11, 1996; Author: Dr. Sundaresan Jayaraman.

Slide Presentation Titled DEfense Logistics Agency Apparel Research Network Sensate Liner Workshop from DLA/ARPA/NRad held Apr. 11, 1996; Author: Donald O'Brien, Technical Enterprise Team.

Slide Presentation Titled TPSS/Senste Liner Technology Development from the DLA/ARPA/NRaD Sensate Liner Workshop held Apr. 11, 1996; Author Dr. Eric J. LInd.

Slide Presentation Titled Smart Textiles from the DLA/ARPA/NRaD Sensate Liner Workshop held Apr. 11, 1996; Author: Dr. Michael Burns, SME, Inc.

Slide Presentation Titled Personal Status Monitor from the DLA/ARPA/NRaD Sensate Liner Workshop held Apr. 11, 1996; Author: Lt. Gen. Peter Kind (Ret.), Sarcos.

Slide Presentation Titled Combat Casualty Care Overview from the DLA/ARPA/NRaD held Apr. 11, 1996; Author: Col. R. Satava ARPA.

Slide Presentation Titled Resources Available Through The Apparel Center At Southern Tech from the Sensate Liner Workshop held Apr. 11, 1996; Author: Dr. Larry Haddock, Southern Tech.

Slide Presentation Titled Introduction: Anthropology Research Project from the DLA/ARPA/NRaD Sensate Liner Workshop held Apr. 11, 1996. Author: Dr. Bruce Bradtmiller.

Slide Presentation Titled Applications For 3D Human Body Modelling from the DLA/ARPA/NRaD Sensate Liner Workshop held Apr. 11, 1996; Author: Dr. Robert M. Beecher, Beecher Research Company.

Slide Presentation Titled Prototype Development of Functional Clothing Research from the DLA/ARPA/NRaD Sensate Liner Workshop held Apr. 11, 1996; Author: Donna Albrecht, Univ. of Wisconsin.

Slide Presentation Titled An Overview of Clemson Apparel Research from the DLA/ARPA/NRaD Sensate Liner Workshop held Apr. 11, 1996; Author: Dr. Chris Jarvis, Clemson Apparel Research.

Slide Presentations from Proposal conference for the Sensate Liner For Combat Casualty Care Program dated Jun. 27, 1996.

* cited by examiner

——— HIGH RESISTANT FIBERS 43
——— BASIC GRID (LOW RESISTANT FIBER) 42
——— DATA BUS 47
• RANDOMLY POSITIONED INTERCONNECTED POINTS 48
——— ELASTIC OPTICAL FIBER SENSOR 41
——— POWER 44
——— GROUND 46

FABRIC OR GARMENT WITH INTEGRATED FLEXIBLE INFORMATION INFRASTRUCTURE

This application claims priority to U.S. provisional patent application 60/085,266, filed on May 13, 1998, now abandoned.

This invention was made with government support under Contract No. N66001-96-C-8639 awarded by the Department of the Navy. The government has certain rights in this invention.

BACKGROUND OF THE INVENTION

1. Field of the Invention

The present invention relates to a fabric or garment, and which includes an integrated infrastructure for collecting, processing, transmitting and receiving information.

2. Background of the Art

Efforts have been made previously to create fabrics and garments which incorporate electrodes for monitoring a condition of the wearer, such as EKG, or conductive fibers for electromagnetic screening. For example, U.S. Pat. Nos. 4,668,545 to Lowe and 5,103,504 to Dordevic disclose fabrics including conductive fibers for electromagnetic screening and for protecting a wearer from magnetic radiation.

U.S. Pat. No. 4,580,572 to Granek et al. discloses a garment for delivering and receiving electric impulses which can include a conductive medium knitted or woven into the cloth, wires sewn onto the cloth or conducting cloth sewn onto non-conducting cloth.

However, these patents fail to disclose either a woven or knitted fabric which incorporates information infrastructure component in the form of a textile fiber which can include a penetration detection component of the fabric for sensing penetration of the fabric or an electrical conductive component of the fabric for collecting or monitoring physical aspects of a wearer of the fabric and which may be worn and hand washed in the same manner as conventional clothing.

A need, therefore, exists for a fabric having an integrated information infrastructure which can be incorporated or fashioned into a wearable garment and which includes a flexible infrastructure for collecting, processing, transmitting and receiving information concerning a wearer of the garment. It is to the provision of such a fabric or garment with an integrated information infrastructure to which the present invention is one aspect directed.

SUMMARY OF THE INVENTION

It is therefore, an object of the present invention to provide a fabric which can be incorporated or fashioned into a garment and which includes intelligence capability, such as the ability to monitor one or more physical conditions, for example body vital signs, and/or penetration of the fabric.

It is another object of the present invention to provide a wearable fabric which includes a flexible information infrastructure for providing such intelligence capability.

It is an additional object of the present invention to be able to provide a full-fashioned garment which can include intelligence capability, such as the ability to monitor one or more body vital signs and/or penetration of the fabric, and a process for making such a garment.

The fabric of the present invention is a tubular woven or knitted fabric, or a woven or knitted two-dimensional fabric, including a flexible infrastructure for collecting, processing, transmitting and receiving information. The fabric can be provided with information collection and processing means, for monitoring one or more physical conditions of the wearer, as well as for monitoring penetration. The physical conditions can include body vital signs, such as heart rate or EKG, pulse and temperature, allergic reactions (such as an anaphylaxis reaction to a bee sting) and voice. The fabric consists of: a base fabric ("comfort component"), and at least one signal transmission component. In one embodiment, the signal transmission component can be either a penetration detection component, or an electrical conductive material component, or both. The preferred penetration detection component is a sheathed plastic optical fiber (POF). The preferred electrical conductive component is a doped nylon fiber with conductive inorganic particles and insulated with PVC sheath, insulated stainless steel fiber, or a thin gauge copper wire with polyethylene sheath. Preferably, the penetration detection component and the electrical conductive component have the characteristics of a textile fiber. By a textile fiber, we mean a unit of matter characterized by flexibility, fineness, a high ratio of length to thickness, high temperature stability and a certain minimum strength and extensibility for textile applications. Optionally, the fabric an include a form-fitting component, such as SPANDEX fiber, or a static dissipating component, such as NEGA-STAT, depending upon need and application. Each of these components can be integrated into the fabric of the present invention and thereby incorporated or fashioned into a wearable intelligent garment.

A "tubular" woven fabric can be produced using plastic optical fibers (POF) or electrical conducting fibers on both. The POF can, among others, serve the following two main functions: (i) It can help detect projectile penetration; and (ii) it can serve as a "data bus" or "motherboard" for transferring information or data to and from other devices that are in communication with it. These capabilities can be used together or individually. The electrical conducting fibers can help to carry information from sensors (mounted on the human/animal body or incorporated into the fabric structure) to monitoring devices to monitor heart rate, breathing rate, voice and/or any other desired body physical property. Thus, the present invention will create a flexible, wearable information infrastructure that will facilitate the "plugging" in of devices for gathering/processing information concerning its wearer utilizing the interconnection of electrical conductive fibers described below. Instead of both POF and conducting fibers, the fabric or garment can incorporate just conducting fibers and not the POF, or vice versa, depending on the desired end-use application. The number, length and pitch (thread spacing) of the POF can be varied to suit the desired end-use requirement. Similarly, the number, length and pitch (thread spacing) of the conducting fibers can be varied to suit the end-use requirement.

This fabric "tube" can be "integrated" into a garment structure such as a regular undershirt or T-shirt, by any appropriate joining technique, such as by sewing, gluing, or attachment by velcro, snaps, zippers, buttons, and the like. The interconnection technology described below can be used to attach connectors to the fabric. Sensors can be incorporated into the fabric and/or mounted on the human being or animal and plugged into connectors incorporated into the fabric. The sensors can be used to monitor one or more body physical signs, such as vital signs. Thus, the fabric or garment of the present invention acts as a useful and flexible information infrastructure for information processing.

In another embodiment of this invention, the POF and/or conducting fibers can be used to knit a tube that can be similarly integrated into a regular knitted garment creating another variation of this infrastructure.

In yet another embodiment of this invention, the POF and/or conducting fibers can be either woven or knitted into a regular two-dimensional fabric. The fabric pieces can then be "integrated" into a three-dimensional garment structure, for example, a T-shirt or undershirt, by any appropriate joining technique, such as sewing, gluing, attachment through velcro, buttons, zippers, and the like. By suitably tapping into the appropriate conducting fibers, the required monitoring capabilities will be created. Alternately, the POF can serve as the "data bus" in place of or in addition to the conductive fibers for various applications.

It can be seen from the description herein of our invention that a fabric is provided which can be incorporated or fashioned into a wearable garment and which includes an integrated flexible infrastructure for collecting, transmitting, receiving and processing information concerning—but not limited to—a wearer of the garment, thus serving as an information infrastructure or "wearable motherboard." These and other objects and advantages of the present invention will become apparent upon reading the following specification and claims in conjunction with the accompanying drawing figures.

DETAILED DESCRIPTION OF THE ILLUSTRATIVE EMBODIMENTS

Figure 1:
FIG. 1 is a front elevational view of a garment into which the wearable fabric with integrated information infrastructure of the present invention has been incorporated.

Referring now to the above figures, wherein like reference numerals represent like parts throughout the several views, the fabric of the present invention having a multi-functional information infrastructure integrated within the fabric for information collection, processing, reception and transmission capability will be described in detail.

The fabric of our present invention is wearable and, thus, provides a wearable information infrastructure integrated within the fabric that has hitherto been typically resident in a computer. When fitted with, or connected to, a data collector(s) such as, but not limited to, a sensor for monitoring body physical signs and connected to a data transmitter or processing unit, as described in detail below, our wearable fabric provides information pathways that allow the sensor to provide information to the transmitter or processor, and vice versa. In this context, the information infrastructure of our fabric invention can manage the transfer of data between the sensor and the transmitter or processing unit. Since the sensor can be considered a "hardware peripheral", our wearable fabric, which can be fashioned into a garment, having an integrated information infrastructure can be conceived of as a "wearable motherboard." When we use the term "wearable motherboard", we are using the term in the context described immediately above.

Figure 2:
FIG. 2 is a front elevational view of another variation of a garment into which the integrated information infrastructure of the present invention has been incorporated.

A. A Fabric Having An Integrated Flexible Information Infrastructure in Accordance with the Present Invention As illustrative generally in FIGS. 1 and 2, the fabric of our present information can be integrated or fashioned into a garment, for example a T-shirt or undershirt, by any appropriate joining technique, such as by sewing, gluing, attachment through VELCRO buttons, zipper, and the like. In the embodiments shown in these figures, the fabric is sewn into an undershirt and a T-shirt, respectively. The fabric provides an infrastructure for a garment for collecting, monitoring, and/or tracking data regarding physical conditions of a wearer of the garment, such as body vital signs or voice, and transmitting such data to a remote location. The fabric can be provided with means in the form of sensors, or connectors for sensors to be worn on the body, for monitoring body physical signs or atmospheric exposure, such as heart rate of EKG, pulse, voice and temperature, blood oxygen levels, chemical exposure levels for any desired chemicals, biological agent exposure levels for desired biological agents, atmospheric smoke levels, atmospheric oxygen levels, radiation exposure, etc. as well as for monitoring penetration. The specific physical or atmospheric quantities monitored depend on the needs of the specific application in which the fabric is being used, e.g. military, medical, firefighting, driving, sports, mountaineering, space, etc.

The fabric with integrated information infrastructure consists of the following components: a base fabric or "comfort component," and an information infrastructure component. The base fabric can be either a tubular woven or knitted fabric, or a two-dimensional woven or knitted fabric, into which the information infrastructure component is incorporated. Additionally, either or both a form-fitting component and a static dissipating component may be included, if desired.

The information infrastructure component can include any or all of the following, individually or in any combination, penetration detection of components, electrically conductive components, sensors, processors, or wireless transmission devices.

1. Woven Fabric

Figure 3:
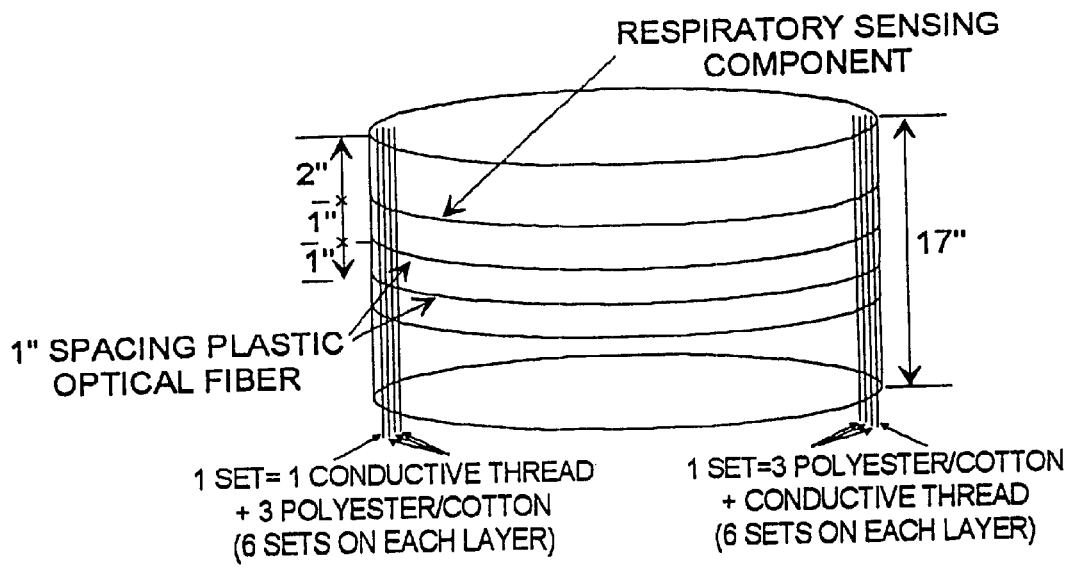
FIG. 3 illustrates a portion of a garment including the integrated information infrastructure according to one embodiment of the present invention.

FIG. 3 illustrates one embodiment of the fabric of the present invention consisting of a woven comfort component of polyester/cotton yarn. A data/power bus for carrying the sensor data or other information is integrated by weaving into the fabric twelve insulated conductive yarns spaced 5 mm apart on either side of the garment. In addition, one of the Respitrace Sensors is woven into the fabric as shown in FIG. 3. The signals from this chest level Respitrace sensor and another woven at the abdomen level are fed directly, or through a PSM (personal status monitor) described in more detail below, to a monitoring device to measure the breathing rate of the wearer. In the case of a temperature sensor, the type of sensor utilized is preferably a standard Thermistor Type Sensor. In the case of a voice sensor a lapel type microphone is preferably used. For EKG sensors, a standard type sensor used in conjunction with typical hospital equipment is preferably used.

Figure 4:
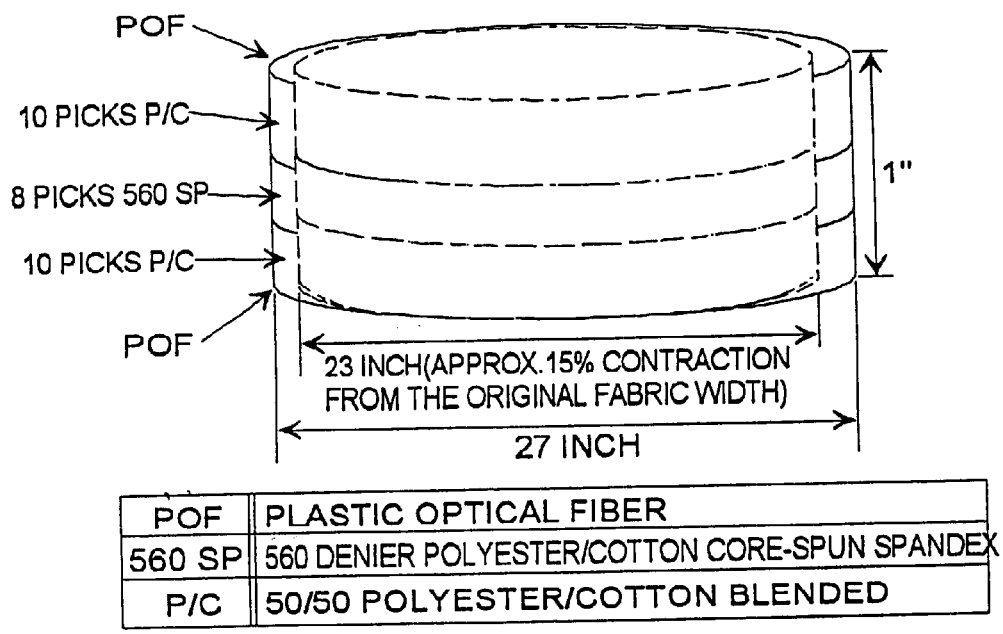
FIG. 4 illustrates a portion of a garment including the integrated information infrastructure according to a second embodiment of the present invention.
Figure 5:
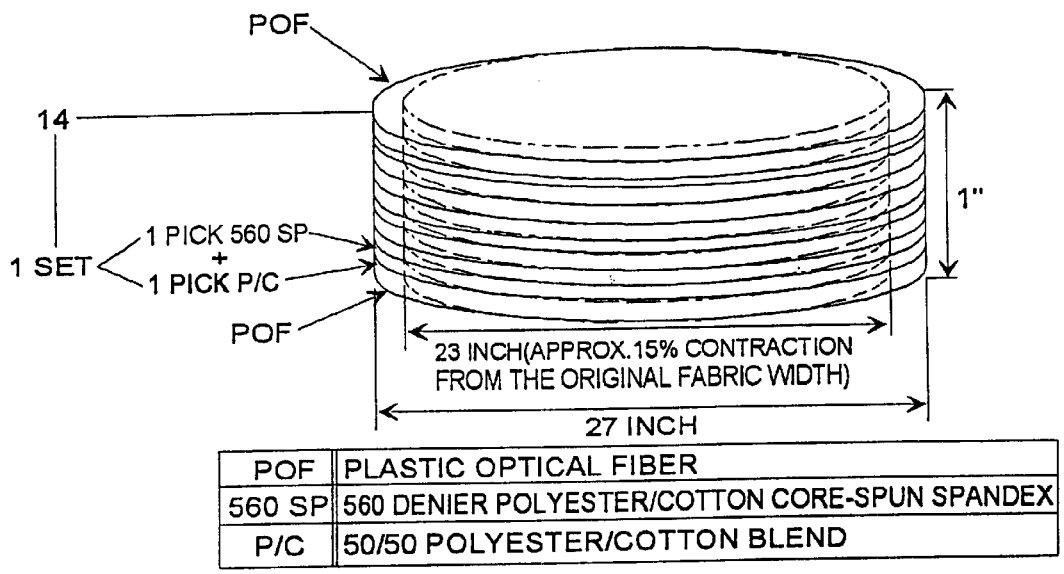
FIG. 5 a portion of a garment including the integrated information infrastructure according to a third embodiment of the present invention.
Figure 6:
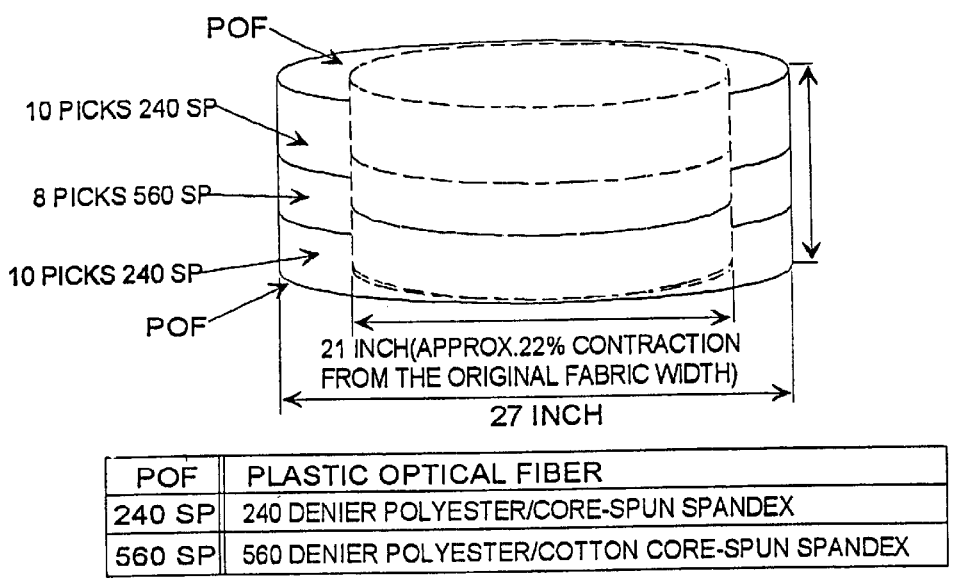
FIG. 6 illustrates a portion of a garment including the integrated information infrastructure according to a fourth embodiment of the present invention.

FIGS. 4–6 illustrate additional embodiments of our fabric consisting of woven designs for form fit. The warp and filling yarns for these designs are given below.

|  | Warp | | Filling | |
|---|---|---|---|---|
|  | Material | EPI | Material | PPI |
| Design I (Fig. 4) | Polyester/ Cotton | 30 560 Denier Core- Spun Span- dex | Polyester/Cotton | 10 |
|  |  |  | Polyester/Cotton | 10 |
| Design II (Fig. 5) | Polyester/ Cotton | 30 560 Denier Core- Spun Span- dex | Polyester/Cotton 14 | 14 |
| Design III (Fig. 6) | Polyester/ Cotton | 30 560 Denier Core- Spun Span- dex | 240 Denier Core-Spun Spandex 8 | 10 |
|  |  |  | 240 Denier Core-Spun Spandex | 10 |

Figure 7:
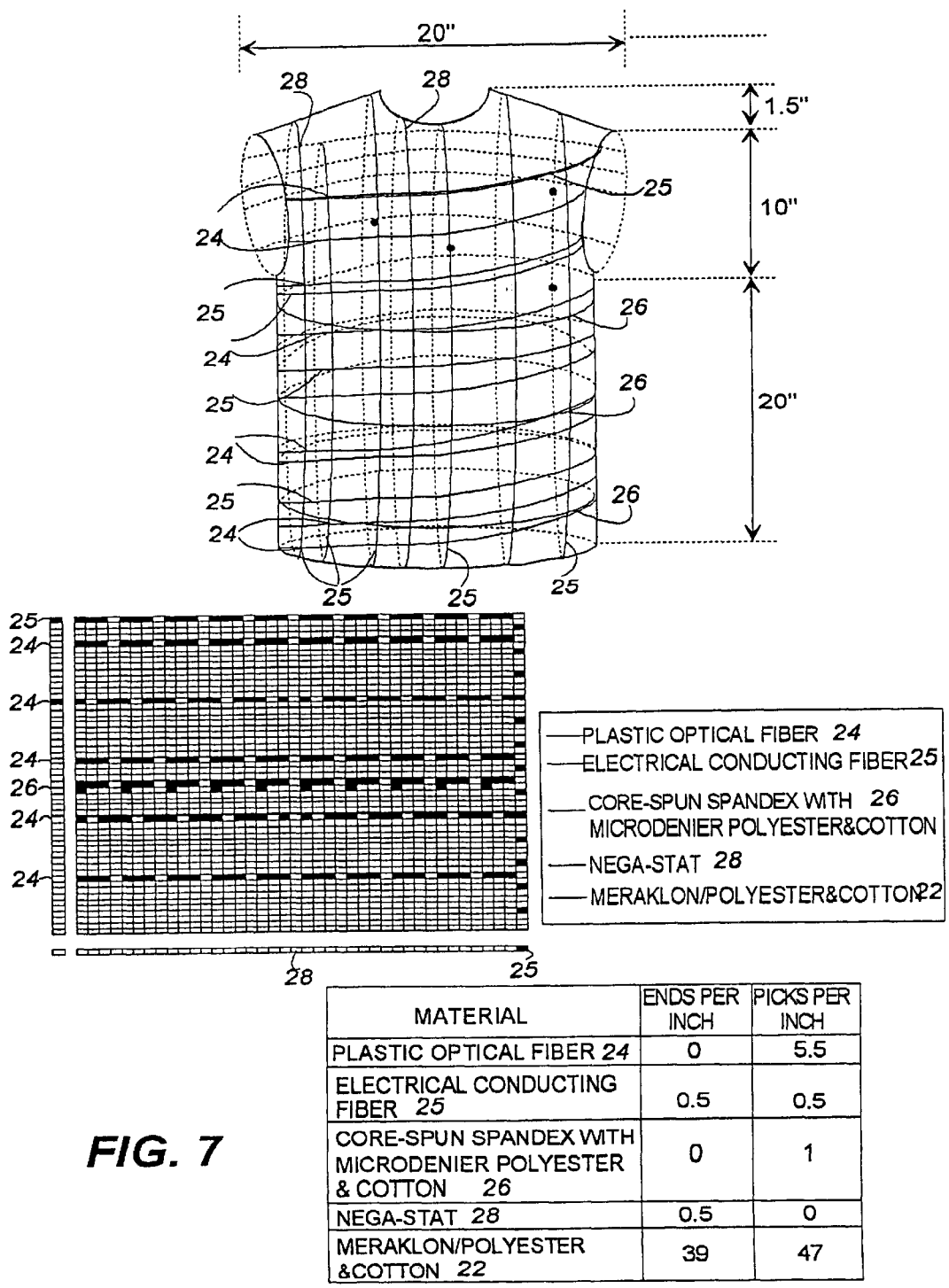
FIG. 7 illustrates a further embodiment of the present invention including the information infrastructure fashioned into a wearable garment.

FIG. 7 shows another representative design of the fabric of the present invention. It consists of a single-piece garment woven similar to a regular sleeveless T-shirt. The legend in the figure denotes the relative distribution of yarns for the various structural components of the fabric in a 2" segment.

The comfort component 22 is the base of the fabric and can in one embodiment be a standard fabric used as component of clothing. The comfort component will ordinarily be in immediate contact with the wearer's skin and will provide the necessary comfort properties for the fabric/garment. Therefore, the chosen material should preferably provide a least the same level of comfort and fit as compared to a typical force used for clothing, e.g., good fabric hand, air permeability, moisture absorption and stretchability.

The comfort component can consist of any yarn applicable to conventional woven fabrics. The choice of material for the yarn will ordinarily be determined by the end use of the fabric and will be based on a review of the comfort, fit, fabric hand, air permeability, moisture absorption and structural characteristics of the yarn. Suitable yarns include, but are not limited to, cotton, polyester/cotton blends, microdenier polyester/cotton blends and polypropylene fibers such as MERAKLON (made by Dawtex Industries).

The fibers preferably suitable for use in the comfort component are MERALON and polyester/cotton blend. MERAKLON is a polypropylene fiber modified to overcome some of the drawbacks associated with pure polypropylene fibers. Its key characteristics in light of the performance requirements are: (a) good wickability and comfort; (b) bulk without weight; (c) quick drying; (d) good mechanical and color fastness properties; (e) non-allergenic and antibacterial characteristics; and (f) odor-free with protection against bacterial growth. Microdenier polyester/cotton blends are extremely versatile fibers and are characterized by: (a) good feel, i.e., handle; (b) good moisture absorption; (c) good mechanical properties and abrasion resistance; and (d) ease of processing. It should be recognized that other fibers meeting such performance requirements are also suitable. Mircodenier polyester/cotton blended fibers are available from Hamby Textile Research of North Carolina. Microdenier fibers for use in the blend are available from DuPont. MERAKLON yarn is available from Dawtex, Inc., Toronto, Canada. In FIG. 7, MERAKLON is shown in both the warp and fill directions of the fabric.

The information infrastructure component of the fabric can include materials 24 for sensing penetration of the fabric 20, or materials 25 for sensing one or more body vital signs, or both. These materials are woven during the weaving of the comfort component of the fabric. After fashioning of the fabric into a garment is completed, these materials can be connected to a monitor (referred to as a "personal status monitor" or "PSM") which will take readings from the sensing materials, monitor the readings and issue an alert depending upon the readings and desired settings for the monitor, as described in more detail below.

Materials suitable for providing generation detection and alert include but are not limited to: silica-based optical fibers, plastic optical fibers, and silicone rubber optical fibers. Suitable optical fibers include those having a filler medium which have a bandwidth which can support the desired signal to be transmitted and required data steams. Silica-based optical fibers have been designed for use in high bandwidth, long distance applications. Their extremely small silica core and low numerical aperture (NA) provide a large bandwidth (up to 500 mhz*km) and low attenuation (as low as 0.5 dB/km). However, such fibers are currently not preferred because of high labor costs of installation and the danger of splintering of the fibers.

Plastic optical fibers (POF) provide many of the same advantages that glass fibers do, but at a lower weight and cost. In certain fiber applications, as in some sensors and medical applications, the fiber length used is so short (less than a few meters) that the fiber loss and fiber dispersion are of no concern. Instead, good optical transparency, adequate mechanical strength, and flexibility are the more important properties and plastic or polymer fibers are preferred. Moreover, plastic optical fibers do not splinter like glass fibers and, thus, can be more safely used in the fabric than glass fibers.

For relatively short lengths, POFs have several inherent advantages over glass fibers. POFs exhibit relatively higher numerical aperture (N.A.), which contributes to their capability to deliver more power. In addition, the higher N.A. lowers the POF's susceptibility to light loss caused by bending and flexing of the fiber. Transmission in the visible wavelengths range is relatively higher than anywhere else in the spectra. This is an advantage since in most medical sensors the transducers are actuated by wavelengths in the visible range of the optical spectra. Because of the nature of its optical transmission, POF offers similar high bandwidth capability and the same electromagnetic immunity as glass filter. In addition to being relatively inexpensive, POF can be terminated using a hot plate procedure which melts back the excess fiber to an optical quality end finish. This simple termination combined with the snap-lock design of the POF connection system allows for the termination of a node in under a minute. This translates into extremely low installation costs. Further, POFs can withstand a rougher mechanical treatment displayed in relatively unfriendly environments. Applications demanding inexpensive and durable optical fibers for conducting visible wavelengths over short distances are currently dominated by POFs made of either poly-methyl-methacrylate (PMMA) or styrene-based polymers.

Silicone rubber optical fibers (SROF), a third class of optical fibers, provide excellent bending properties and elastic recovery. However, they are relatively thick (of the order of 5 mm) and suffer from a high degree of signal attenuation. Also, they are affected by high humidity and are not yet commercially available. Hence, these fibers are not currently preferred for use in the fabric.

In FIG. 7, the POF 24 is shown in the filling direction of the fabric, though it need not be limited to only the filling direction. To incorporate the penetration sensing component material into a tubular woven fabric, the material, preferably plastic optical fiber (POF), is spirally integrated into the structure during the full-fashioned weaving fabric production process as described in copending U.S. patent application Ser. No. 09/157,607, which is incorporated herein in its entirety as if fully set forth herein. The POF continues throughout the fabric without any discontinuities. This results in only one single integrated fabric and no seams are present in the garment. The preferred plastic optical fiber is from Toray Industries, New York, in particular product code PGS—FB250 optical fiber cord.

Alternatively, or additionally, the information infrastructure component may consist of either a high or a low conductivity fiber electrical conducting material component (ECC) 25. The electrical conductive fiber preferably has a resistivity of from about $0.07 \times 10^{-3}$ to 10 kohms/cm. The ECC 25 can be used to monitor one or more body vital signs including heart rate, pulse rate and temperature through sensors on the body and for linking to a personal status monitor (PSM). Suitable materials include the three classes of intrinsically conducting polymers, doped inorganic fibers and metallic fibers, respectively.

Polymers that conduct electric currents without the addition of conductive (inorganic) substances are known as "intrinsically conductive polymers" (ICP). Electrically conducting polymers have a conjugated structure, i.e., alternating single and double bonds between the carbon atoms of the main chain. In the late 1970s, it was discovered that polyacetylene could be prepared in a form with a high electrical conductivity, and that the conductivity could be further increased by chemical oxidation. Thereafter, many other polymers with a conjugated (alternating single and double bonds) carbon main chain have shown the same behavior., e.g, polythiophene and polypyrrole. Initially, it was believed that the processability of traditional polymers and the discovered electrical conductivity could be combined. However, it has been found that the conductive polymers are rather unstable in air, have poor mechanical properties and cannot be easily processed. Also, all intrinsically conductive polymers are insoluble in solvents and they possess a very high melting point and exhibit little other softening behavior. Consequently, they cannot be processed in the same way as normal thermoplastic polymers and are usually processed using a variety of dispersion methods. Because of these shortcomings, fibers made up of fully conducting polymers with good mechanical properties are not yet commercially available and hence are presently preferred for use in the fabric.

Yet another class of conducting fibers consists of those that are doped with inorganic or metallic particles. The conductivity of these fibers is quite high if they are sufficiently doped with metal particles, but his would make the fibers less flexible. Such fibers can be used to carry information from the sensors to the monitoring unit if they are properly insulated.

Metallic fibers, such as copper and stainless steel insulated with polyethylene or polyvinyl chloride, can also be used as the conducting fibers in the fabric. With their exceptional current carrying capacity, copper and stainless steel are more efficient than any doped polymeric fibers. Also, metallic fibers are strong and they resist stretching, neck-down, creep, nicks and breaks very well. Therefore, metallic fibers of very small diameter (of the order of 0.1 mm) will be sufficient to carry information from the sensors to the monitoring unit. Even with insulation, the fiber diameter will be less that 0.3 mm and hence these fibers will be very flexible and can be easily incorporated into the fabric. Also, the installation and connection of metallic fibers to the PSM unit will be simple and there will be no need for special connectors, tools, compounds and procedures. One example of a high conductive yarn suitable for this purpose is BEKINOX available from Bekaert Corporation, Marietta, Ga., a subsidiary of Bekintex NV, Wetteren, Belgium, which is made up of stainless steel fibers and has a resistivity of 60 ohm-meter. The bending rigidity of this yarn is comparable to that of the polyamide high-resistance yarns and can be easily incorporated into the information infrastructure in our present invention.

Thus, the preferred electrical conducting materials for the information infrastructure component for the fabric are: (i) doped nylon fibers with conductive inorganic particles and insulated with PVC sheath; (ii) insulated stainless steel fibers; and (iii) thin gauge copper wires with polyethylene sheath. All of these fibers can readily be incorporated into the fabric and can serve as elements of an elastic printed circuit board, described below. An example of an available conducting fiber is X-Static coated nylon with PVC insulation (T66) form Sauquoit Industries, Scranton, Pa. An example of an available thin copper wire is 24 gauge insulated copper wire from Ack Electronics, Atlanta, Ga.

Figure 17:
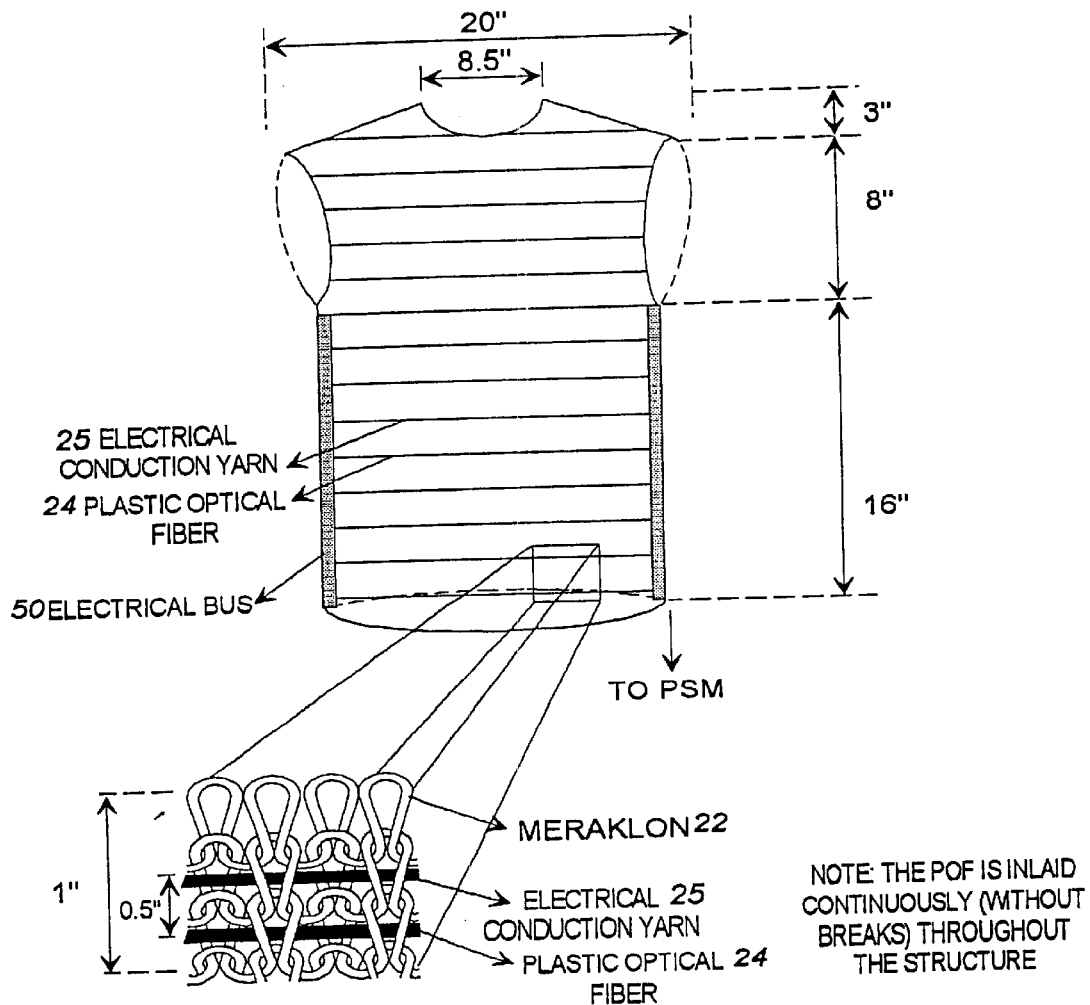
FIG. 17 illustrates a knitted sample of the present invention.
Figure 18:
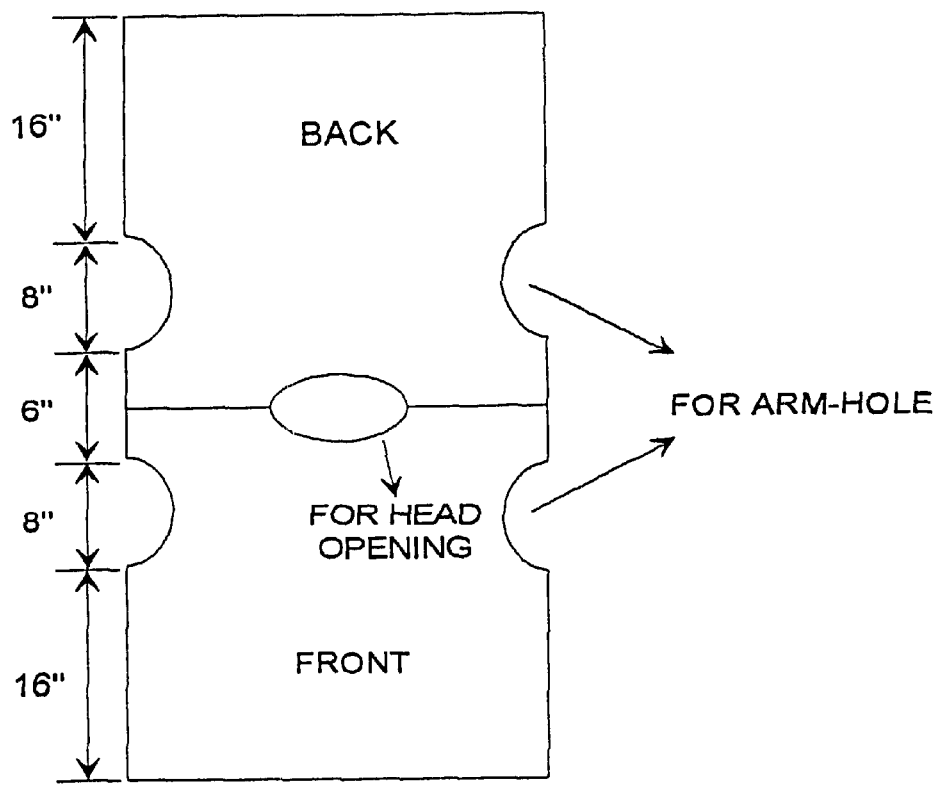
FIG. 18 illustrates an opened out illustration of the garment of FIG. 17.

The electrical conducting component fibers 25 can be incorporated into the woven fabric in two ways: (a) regularly spaced yarns acting as sensing elements; and (b) precisely positioned yarns for carrying signals from the sensors to the PSM. They can be distributed both in the warp and filling directions in the woven fabric. Additionally the fabric/garment including the information infrastructure can be knitted, as opposed to being woven, as shown in FIGS. 17 and 18.

The form-fitting component (FFC) 26 provides form-fit to the wearer, if desired. More importantly, it keeps the sensors in place on the wearer's body during movement. Therefore, the material chosen should have a high degree of stretch to provide the required form-fit and at the same time, be compatible with the material chosen for the other components of the fabric. Any fiber meeting these requirements is suitable. The preferred form-fitting component is Spandex fiber, a block polymer with urethane groups. Its elongation at break ranges from 500 to 600% and, thus, can provide the necessary form-fit to the garment. Its elastic recovery is also extremely high (99% recovery from 2–5% stretch) and its strength is in the 0.6–0.9 grams/denier range. It is resistant to chemicals and withstands repeated machine washings and the action of perspiration. It is available in a range of linear densities.

The SPANDEX band 26 shown in the filling direction in FIGS. 4 and 6 is the FFC for the tubular woven fabric providing the desired form-fit. These bands behave like "straps", but are unobtrusive and are well integrated into the fabric. There is no need for the wearer to tie something to ensure a good fit for the garment. Moreover, the SPANDEX band will expand and contract as the wearer's chest expands and contracts during normal breathing.

The purpose of the static dissipating component (SDC) 28 is to quickly dissipate any built-up static charge during the usage of the fabric. Such a component may not always be necessary. However, under certain conditions, several thousand volts may be generated which could damage the sensitive electronic components in the PSM Unit. Therefore, the material chosen must provide adequate electrostatic discharge protection (ESD) in the fabric.

NEGA-STAT, a biocomponent fiber produced by DuPont is the preferred material for the static dissipating component (SDC). It has a trilobal shaped conductive core that is sheathed by either polyester or nylon. This unique trilobal conductive core neutralizes the surface charge on the base material by induction and dissipates the charge by air ionization and conduction. The nonconductive polyester or nylon surface of NEGA-STAT fiber controls the release of surface charges from the thread to provide effective static control of material in the grounded or ungrounded applications according to specific end-use requirements. The outer shell of polyester or nylon ensures effective wear-life performance with high wash and wear durability and protection against acid and radiation. Other materials which can effectively dissipate the static charge and yet function as a component of a wearable, washable garment may also be used.

Referring again to FIG. 7, the NEGA-STAT fiber 28 running along the height of the shirt, in the warp direction of the fabric, is the static dissipating component (SDC). The proposed spacing is adequate for the desired degree of static discharge. For the woven tubular garment, it will ordinarily, but not necessarily, be introduced in the warp direction of the fabric.

Figure 8:
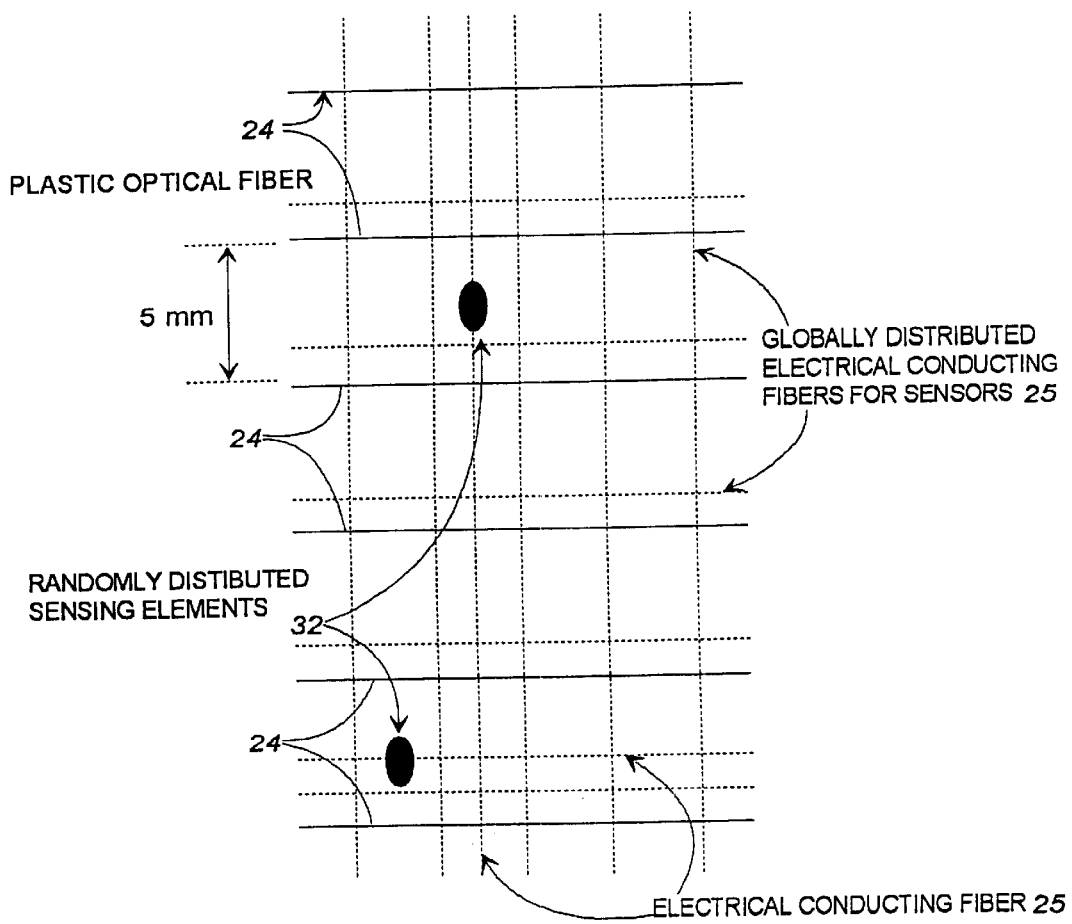
FIG. 8 illustrates the distribution of sensors in the garment of FIG. 7.
Figure 11:
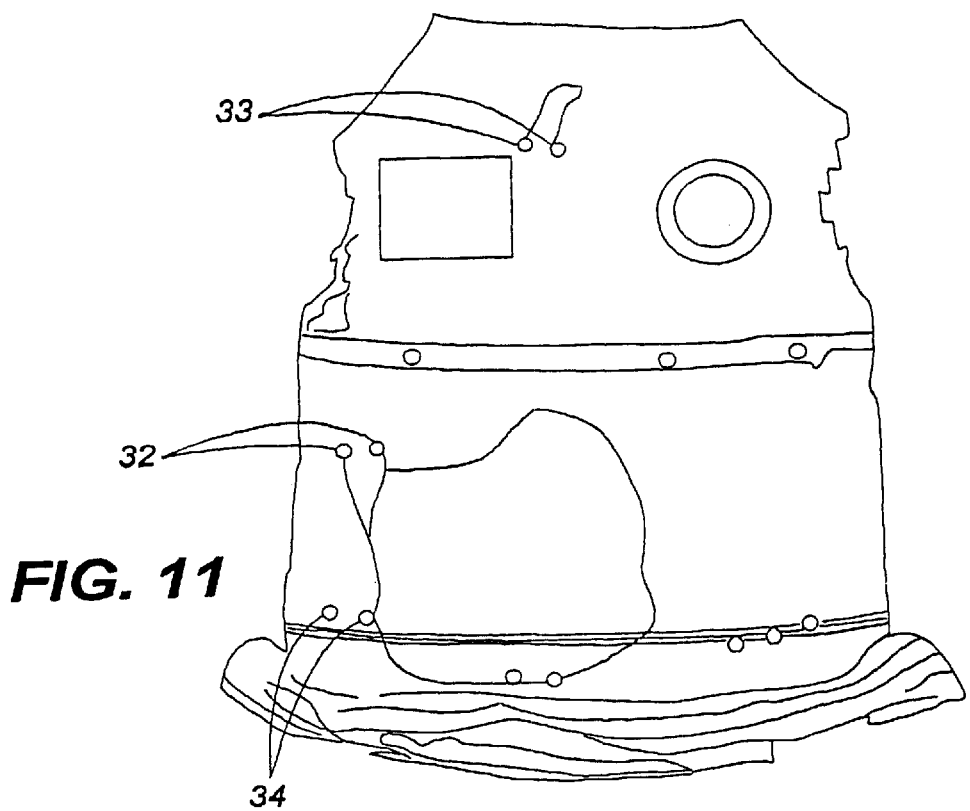
FIG. 11 illustrates a full-fashioned garment with a temperature sensor and microphone integrated using T-connectors according to the present invention.

With reference to FIG. 8, connectors (not shown), such as T-connectors (similar to the "button clips" used in clothing), can be used to connect the body sensors 32 and/or microphone (not shown) to the conducting wires that go to the PSM. By modularizing the design of the fabric 20 (using the connectors), the sensors 32 themselves can be made independent of the fabric 20. This accommodates different body shapes. The connector makes it relatively easy to attach the sensors to the wires. This is illustrated in FIG. 11 where the microphone 33 is attached to the garment by snapping it into the T-Connectors 34. FIG. 11 also shows the thermistor sensor 32 "plugged" into the garment. Yet another advantage of separating the sensors themselves from the garment, is that they need not be subjected to laundering when the garment is laundered, thereby minimizing any damage to them. However, it should be recognized that the sensors 32 can also be woven into the structure.

The specification for the preferred materials to be used in the production of our fabric/garment are as follows:

| Component | Materials | Count (CC) |
|---|---|---|
| Penetration Sensing (PSC) | Plastic Optical Fibers (POF) | PVC sheathed POF |
| Comfort (CC) | MERKALON Microdenier Poly/Cotton Blend | 18sNe |
| Form-fitting (FFC) | SPANDEX | 6s Ne Core-Spun from 560 denier SPANDEX yarn |
| Global and Random Conducting (ECC) | X-static Nylon with PVC insulation | 6s Ne |
| | Stainless Steel | 110 Tex |
| Static Dissipating (SDC) | NEGA-STAT | 18s Ne |

Figure 16:
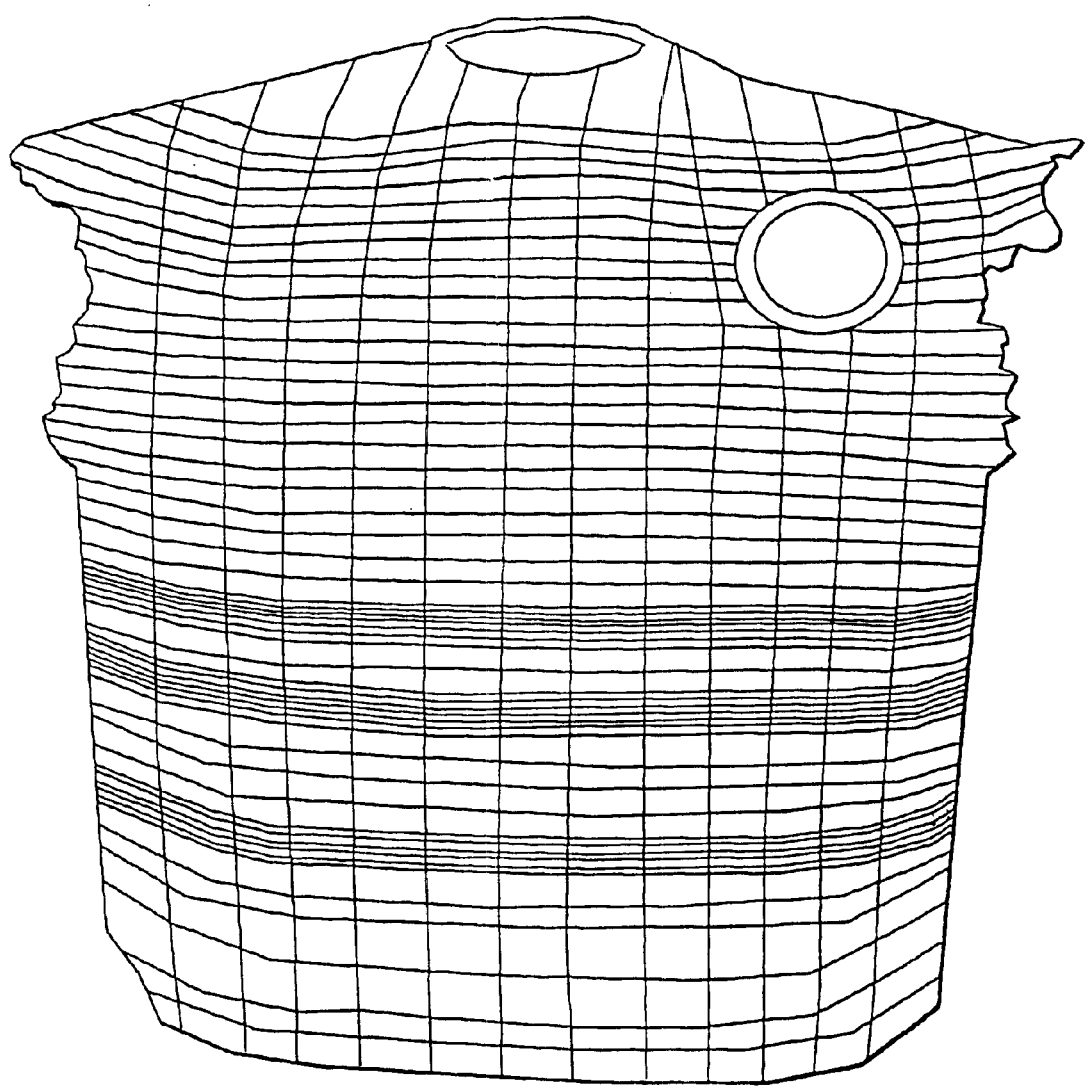
FIG. 16 illustrates a woven fabric of the present invention integrated with sensors.

The yarn counts have been chosen based on initial experimentation using yarn sizes that are typically undergarments. Other yarn counts can be used. FIG. 7 also shows the specifications for the tubular woven fabric. The weight of the fabric is around 8 oz/yd$^2$ or less. FIG. 16 shows the fabric of FIG. 7 with integrated sensors interconnected using the technology illustrated in FIGS. 9 and 11.

| Parameter | Details |
|---|---|
| Knitting Machine Description | Flat Bed (Hand Operated) |
| | 1 × 1 Rib |
| Gauge (Needles Per Inch) | 5 |
| Width | 40 Inches |
| Plastic Optical Fiber | PGU-CD-501-10-E from Toray Industries, New York. |
| Electrical Conductive Fiber | X-Static Conducting Nylon fiber with insulated PVC Sheath from Sauquoit Industries, Pennsylvania |
| Meraklon | 2/18s Ne Yarn from Dawtex, Inc., Canada |

The above table shows the parameters used for producing the knitted fabric embodiment of our present invention having an information infrastructure integrated within the fabric. FIG. 17 shows the structure of the garment in which the Plastic Optical Fiber (POF) 24 is continuously inlaid throughout the structure. Thus, there is one single POF traversing the entire structure. The Electrical Conductive Yarn 25 is also inlaid in the structure. The comfort component, Meraklon 22 forms the 1×1 rib structure and serves as the base of the fabric. The electrical bus 50 in the structure is also shown. In this embodiment, the electrical bus 50 has been knitted separately and attached to the structure.

Figure 19:
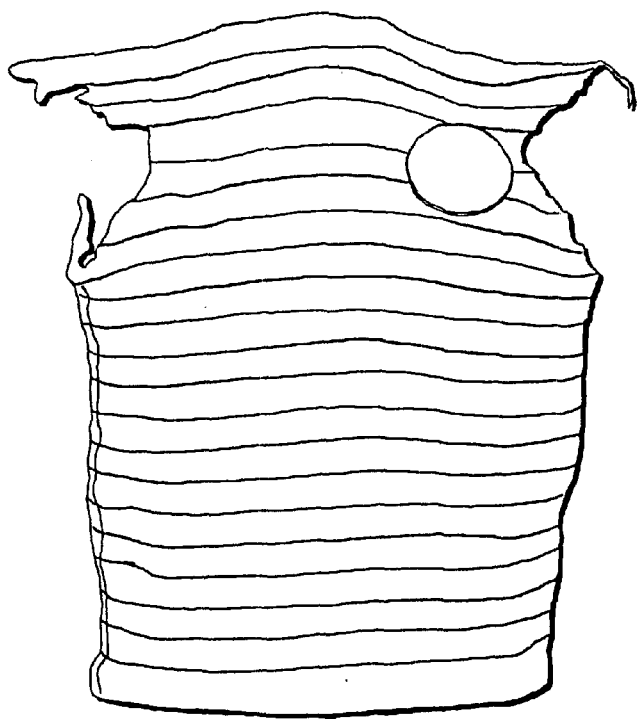
FIG. 19 is a front view of a knitted fabric according to one embodiment of the present invention.
Figure 20:
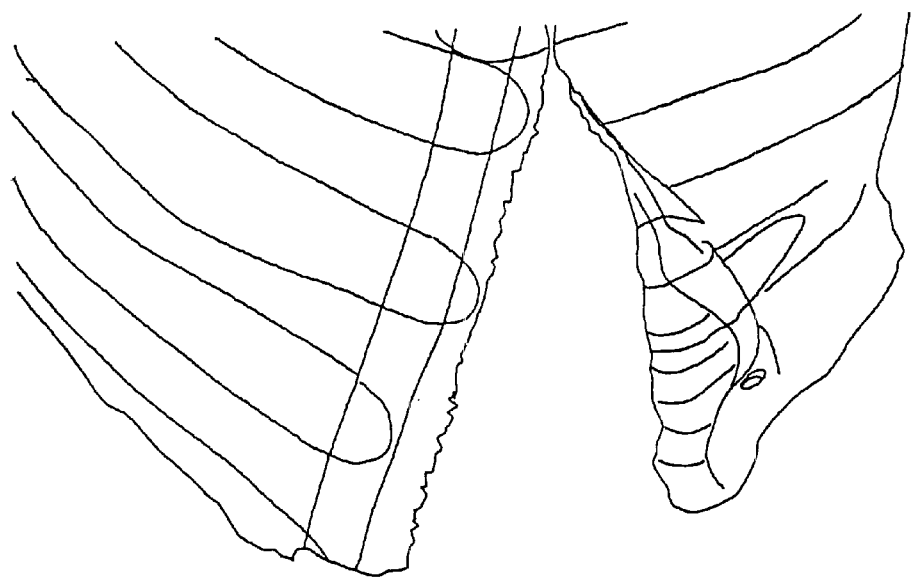
FIG. 20 illustrates one style of attachment for the invention of FIG. 19.
Figure 21:
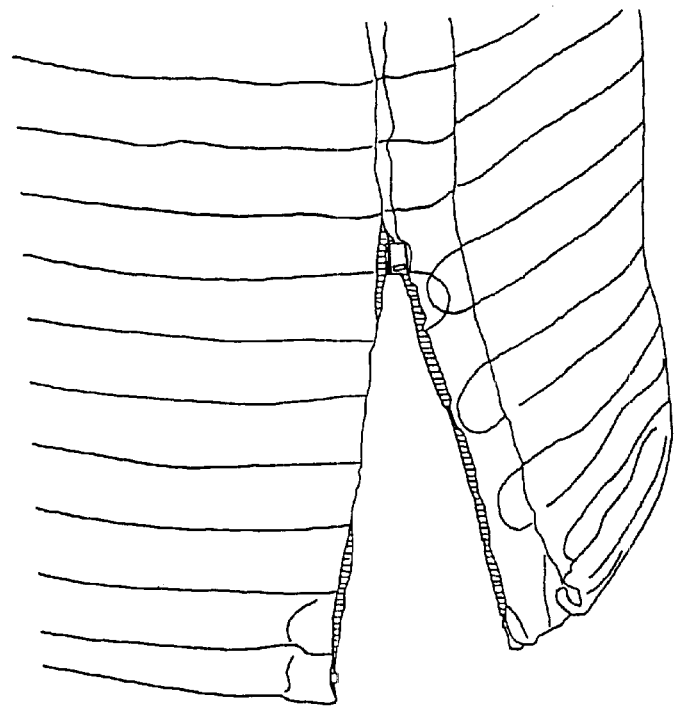
FIG. 21 illustrates another style of attachment for the invention of FIG. 19.

FIG. 18 shows an opened out image of the single piece integrated structure in FIG. 17. A front-view of the knitted fabric is shown in FIG. 19. A close-up view of the Velcro attachment used to bind the front and back of the garment is shown in FIG. 20. The use of zippers to bind the front and back of the garment is shown in FIG. 21. In the embodiments shown in FIGS. 20 and 21, the electrical bus has been knitted separately and bound to the front and back of the garment. The embodiments of FIGS. 20 and 21 can also be used for attachment of a woven garment as well as the knitted garment, in the same manner as described.

B. Protection of the Plastic Optical Fiber in the Fabric/Garment Having An Integrated Information Infrastructure Some plastic optical fibers may be somewhat stiff allowing a limited bending radius and which may be more difficult to weave or knit into the fabric of our invention. A preferred POF is one having polymethyl methyacrylate as its core material and a core diameter of about 225–255 microns, a fluorinated polymer as its cladding material with a cladding diameter of about 235–265 microns. The preferred POF also has a numerical aperture of about 0.05 mm, a tensile strength (yield point) of about 0.3 kg, an allowable bending radius of about 9 mm and an attenuation of approximately 0.18 dB/m (650 nm).

To protect the bare POF and to protect the wearer from the POF, a sheath for the POF is desirable. The preferred sheath material is one that is flexible and would not irritate the skin of the wearer when it comes into contact with the wearer. PVC is a suitable sheath material. The preferred sheath diameter is equal to the diameter of the POF plus 0.5 to 1.0 mm, providing a sheath thickness of 0.25 mm and an outer diameter of 1.5 mm. The sheath material may either be transparent or opaque. The advantages of a transparent sheath material include: points of damage along the POF caused during usage or manufacturing can be visually identified; the intensity of light transmitted throughout the POF can be monitored; and, if desired for certain applications, glowing of the POF can be viewed.

The sheath can be sleeved over the POF either continuously or intermittently, either manually or mechanically. It can also be sleeved in segments with the segment lengths varied.

C. Interconnection of Electrical Conductive Fibers

Interconnection of electrical conductive fibers incorporated into the fabric can be achieved by the following sequence of operations:

1. Softening and removal of the insulation of the electrical conductive fibers at the desired intersection zone;

2. Abrasion of insulation at the intersection zone;

3. Application of a conductive polymer paste at the intersection zone to establish the interconnection between the electrical conductive fibers;

4. Insulation of the interconnect zone to prevent undesirable short circuits; and 5. If desired, attachment of sensor or connector.

The potential for automation has been a key driving factor in the development of the interconnection process since automation is essential for large scale production of the fabric/garment. Also, automation is preferred for the reproducibility and repeatability of the various steps to create a uniform product on a continuous basis. The details of the various steps are presently discussed.

1. Softening and Removal of Insulation

In order to make a connection of intersecting electrical conductive fibers, the insulation at the intersection must first be removed. This can be done by any one of a number of ways. Suitable removable techniques include chemical etching, mechanical removal and any spot welding technique such as ultrasonic welding, laser light application or other localized heating technique. Preferably, the interconnection zone is chemically softened for the effective removal of the insulation, such as vinyl sheath. The process variables are: (i) the chemical used in the process; (ii) the concentration of the chemical; (iii) the amount of chemical applied; and (iv) duration of chemical application. Acetone has been found to work quite well as a chemical-softening agent. A few drops of Acetone are applied. It is allowed to stand for about 10 seconds before the next step in the process. These processing conditions ensure that the conductive yarn itself is not damaged. Also since polyester, cotton and SPANDEX do not interact with acetone, they are not damaged during this process. Where stainless steel is used as the electrical conductive fiber, heat alone may be sufficient to achieve the desired softening and removal of insulation.

2. Abrasion of Insulation

Figure 9:
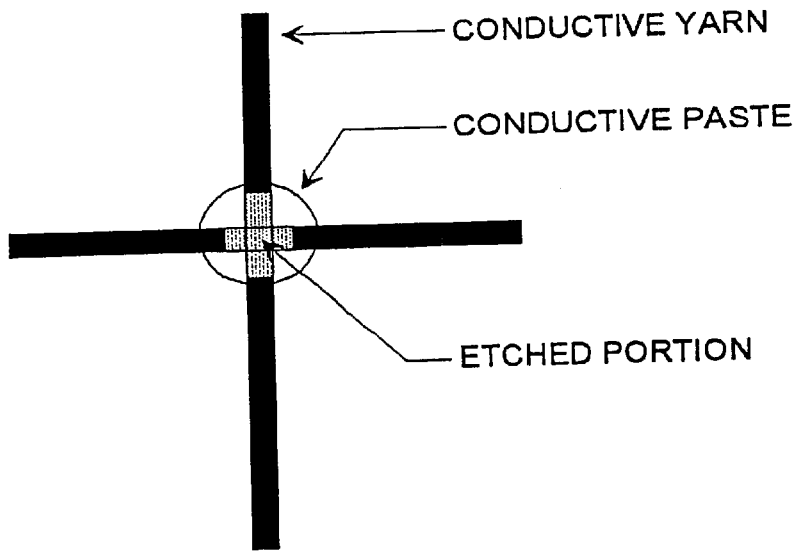
FIG. 9 illustrates another aspect of the present invention, namely, the interconnection of intersecting electrically conductive fibers in fabric of a preferred embodiment of the present invention.

The next step, if needed, is to abrade the insulation at the intersection zone that has been softened. A vibrating brush can be used, preferably one that oscillates at 3000 Hz. This effectively strips out the insulation at the interconnection zone as shown in FIG. 9. The process variables are: (i) the frequency of oscillation of the brush; (ii) the pressure applied during abrasion; and (iii) duration of abrasion. By modifying these parameters, it would be possible to strip out different types of insulation without damaging the conductive yarns themselves. Depending on the method used for removal of insulation, it may or may not be necessary to carry out this step. Some methods of removal may result in removal of sufficient amount of insulation such that this abrasion step would not be needed.

3. Application of Conductive Paste

The interconnection between the conductive yarns where the insulation has been removed can be established by applying a conductive paste to close the circuit between the conductive yarns. The process variables are: (i) the properties of the conductive paste used in the process; and (ii) the quantity of the paste applied to the interconnect zone. The conductive paste should be chosen such that it offers only minimum electrical resistance, adheres well to the conductive yarns, and does not chemically react with the conductive yarn. Based on these requirements, Magnolia 3870, a silver-filled epoxy, room temperature curing paste, is a preferred conducting paste. It has a shear strength of 2000 psi at 75° F. and has a resistivity of 0.004 ohm-cm at 75° F. It also cures well at room temperature and does not react with the polyamide conductive yarn. It can be applied to the interconnect zone using a grease gun or a similar device.

4. Insulation of the Interconnection Zone

The interconnection zone must be insulated to prevent it from shorting in the presence of water. A polyester/urethane based resin can be used to insulate the interconnection zone. The insulating layer should not chemically react with the conductive paste, should adhere well to the paste and should offer adequate insulation. It can be applied to the interconnection zone using a brush or other application means.

5. Attachment of a Sensor or Sensor Connector

Figure 10:
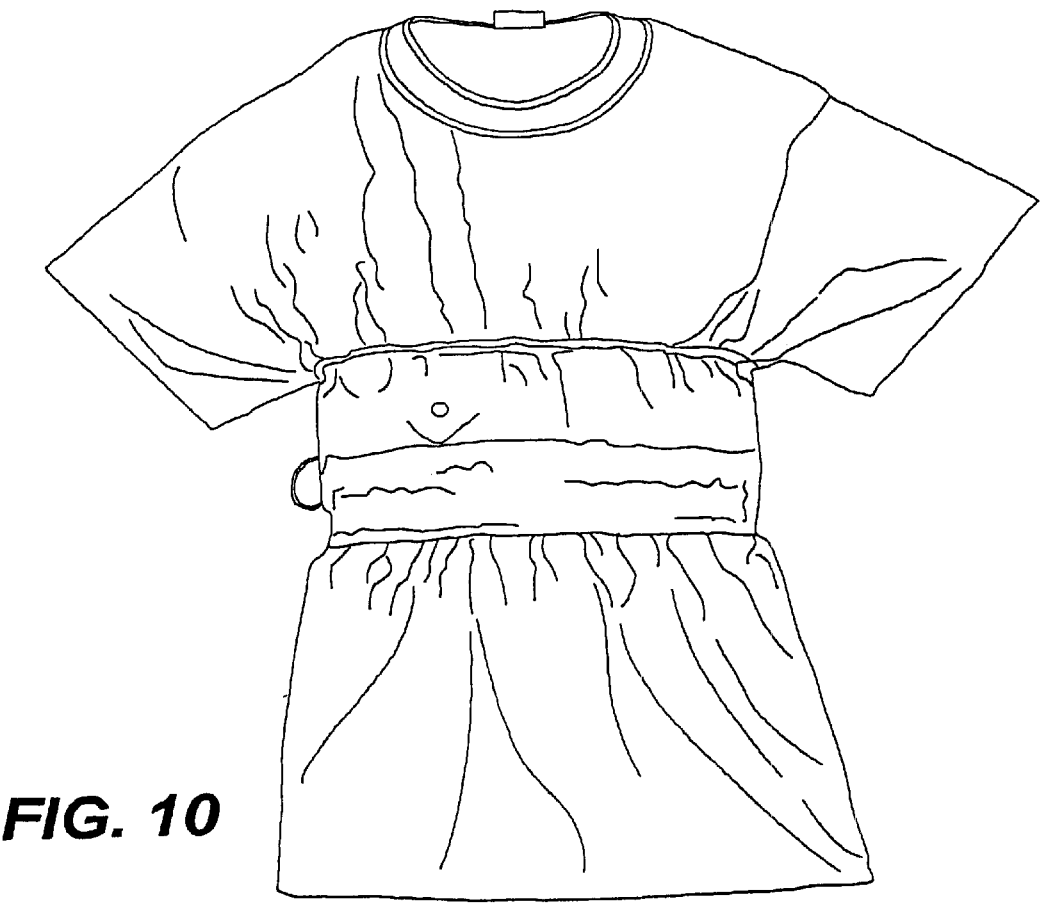
FIG. 10 illustrates a garment incorporating the fabric of the present invention onto which a T-connector has been connected to electrically conductive fibers using the interconnection technology of FIG. 9 and to which an EKG sensor has been attached.
Figure 12:
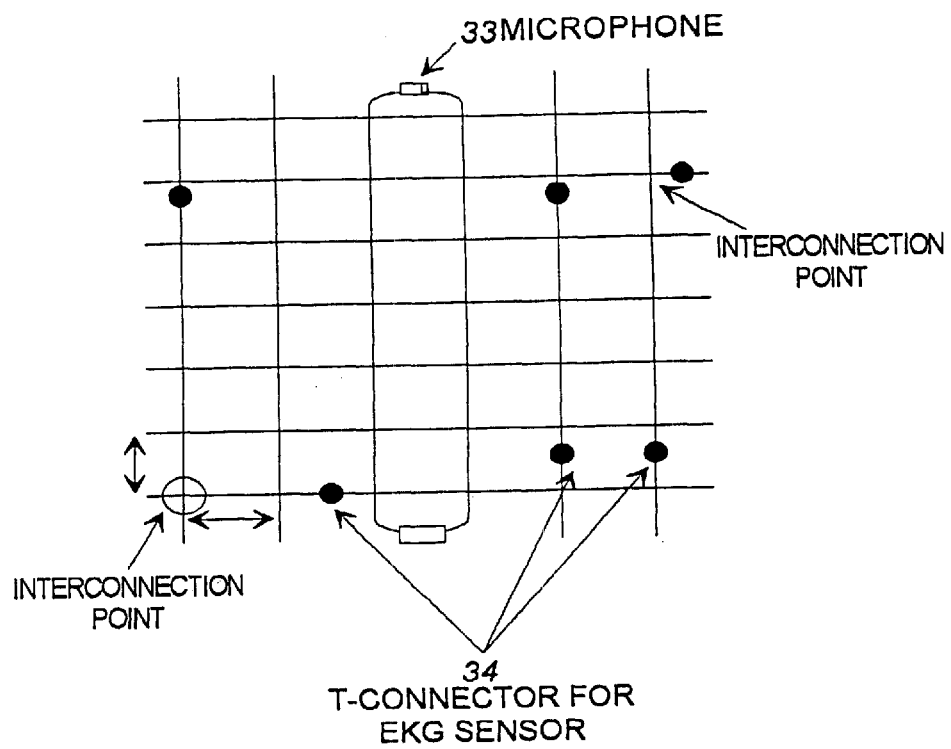
FIG. 12 illustrates a detailed view of the results of using the interconnection technology of FIG. 9 of the present invention.
Figure 13:
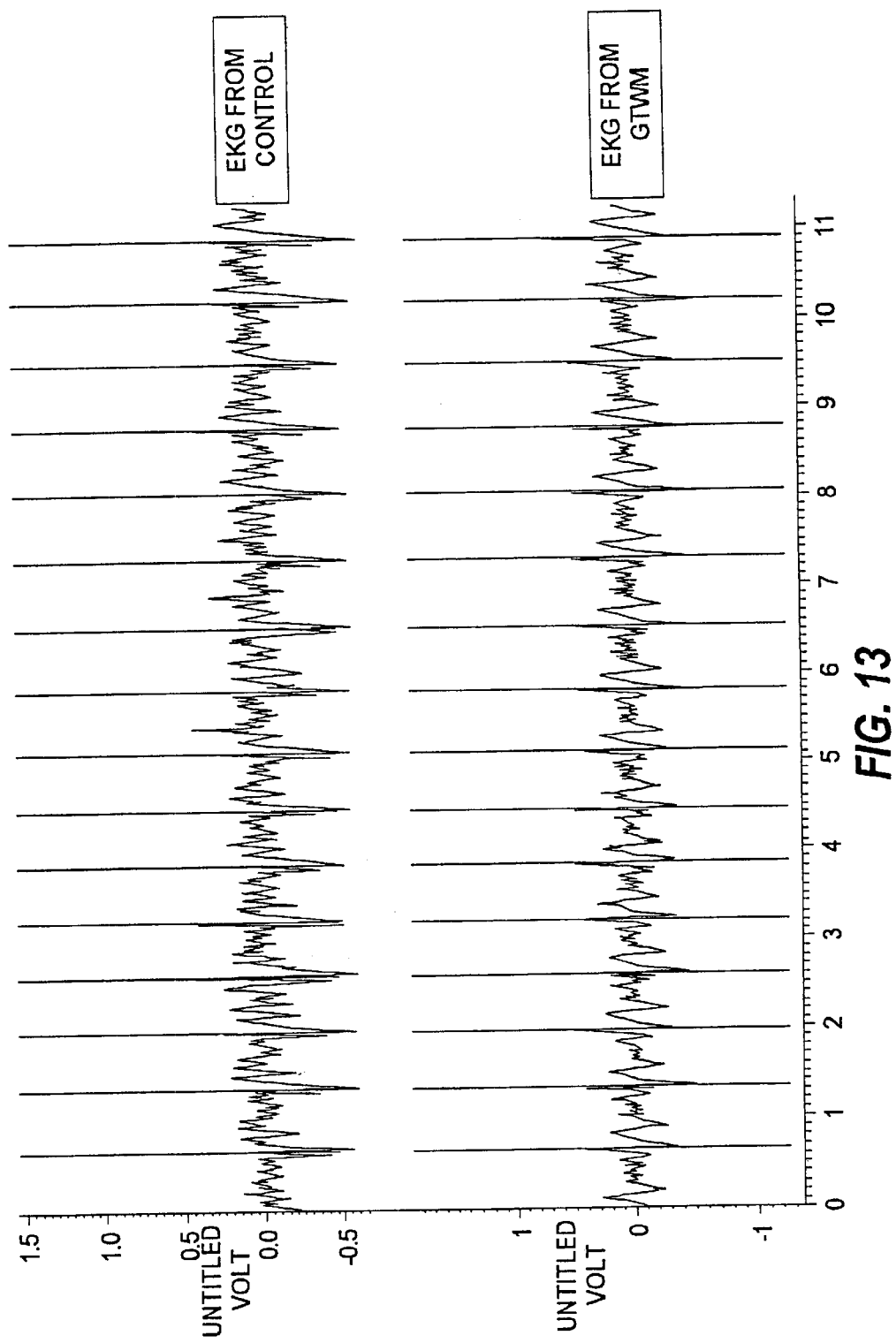
FIG. 13 illustrates an EKG trace taken from an EKG sensor incorporated into the garment of FIG. 10.

Additionally, if desired, either a sensor or a sensor connector, such as a T-connector, can be attached to the interconnection zone. FIGS. 10, 11 and 12 show the attachment of a T-connector 34 to the fabric for connecting a sensor, such as an EKG sensor or a microphone 33 to the fabric. FIG. 13 shows an EKG trace taken from EKG sensors attached to the garment of FIG. 11 worn by a person.

If desired, the interconnection technology and T-Connectors can be used to mount antennas in a phased array formation on the garment. Groups of individuals wearing the said garment with mounted antennas can form a large phased array to track moving objects such as aircraft.

Yet another modification is to provide a keyboard capability in the garment using either the conducting fibers themselves or through sensors mounted on the conducting fibers using the interconnection technology so that the keyboard can serve as an input device for the information processing and monitoring devices plugged into the fabric of our present invention.

D. Core Spinning Technology

Core spinning is the process of sheathing a core yarn (e.g. POF or SPANDEX yarns) with sheath fibers (e.g., MERAKLON or Polyester/Cotton). It is not required in all situations for the present invention. It is desirable when the information infrastructure component, or other components other than the comfort component, do not possess the comfort properties that are desired for the garment. There are two ways to core spin yarns—one using modified ring spinning machines and another by using a friction-spinning machine. Ring spinning machines are very versatile and can be used for core spinning both fine and coarse count yarns. However, the productivity of the ring-spinning machine is low and the package sizes are very small. Friction spinning machines can be used only to produce coarse count yarns, but the production rates and the packages sizes are much higher than ring spinning. Where the yarns that are used are relatively coarse, friction-spinning technology is preferred for core spinning the yarns.

The preferred configuration of the friction-spinning machine for producing core spun yarns is as follows:

| Parameter | Details |
| --- | --- |
| Machine Model | DREF3 ® |
| Machine Description | Friction Core Spinning Machine |
| Draft | 200 |
| Speed | 170 m/min |
| Number of Doublings | 5 |
| Drafting Mechanism Type | 3/3 |
| Core-Sheath Ratio | 50:50 |

Figure 14:
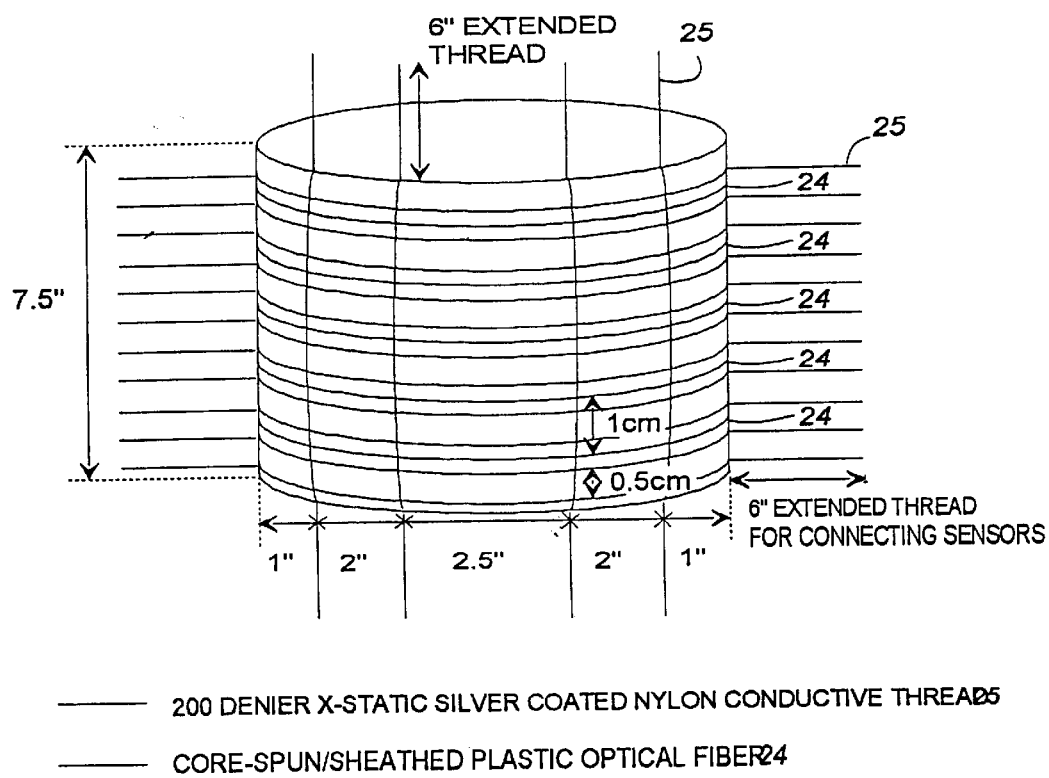
FIG. 14 illustrates a woven sample of the fabric of FIG. 7.
Figure 15:
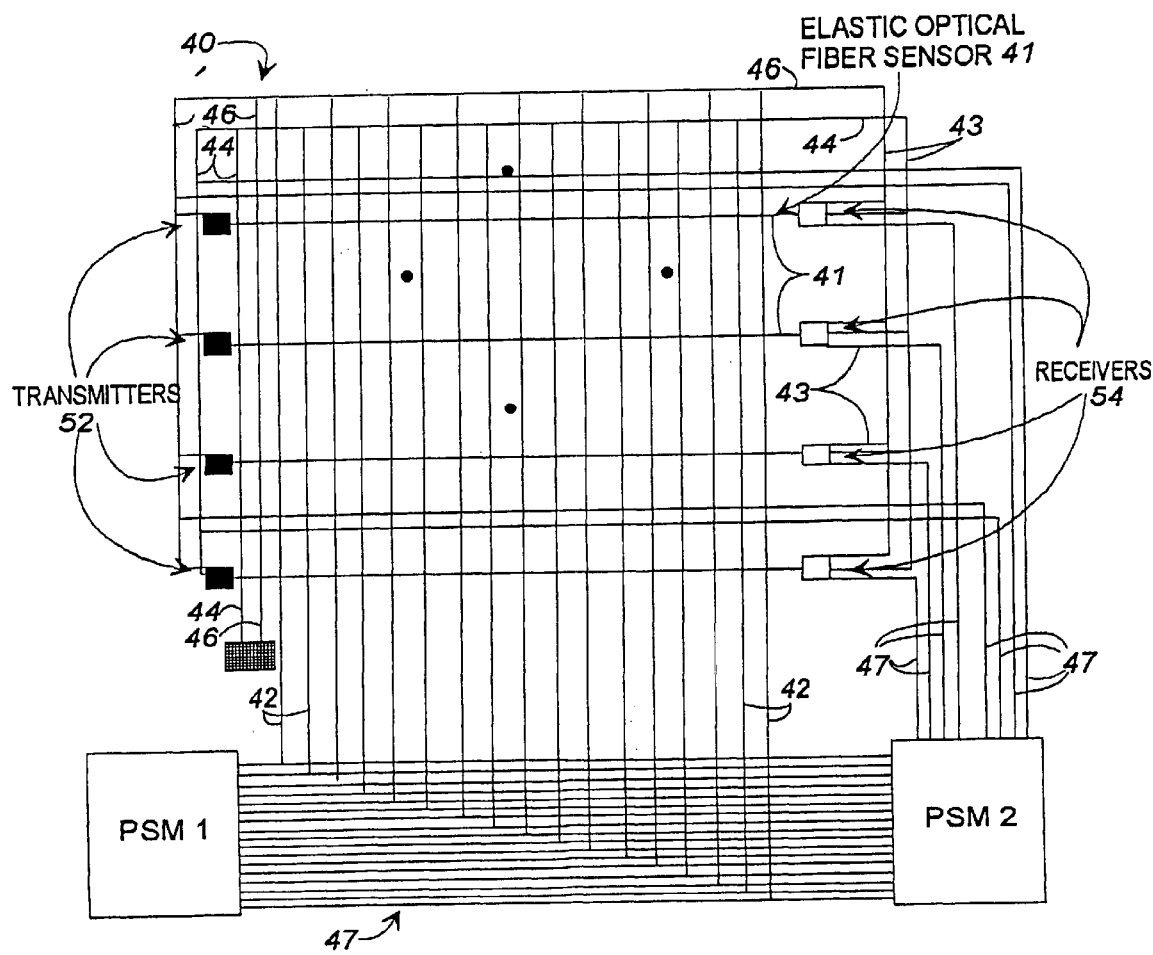
FIG. 15 illustrates the invention of FIG. 7 in the form of a printed elastic board.

Four full-scale prototypes of a garment fashioned form out fabric were produced on the AVL-Dobby loom. Additionally, two samples of a woven fabric were produced on a tabletop loom. The specifications for the samples are shown in FIG. 14. These samples were designed with high 42 and low 43 conductive electrical fibers spaced at regular intervals to act as an elastic circuit board 40. The circuit diagram of this board is illustrated in FIG. 15. The figure shows the interconnections between the power 44 and ground 46 wires and high 42 and low 43 conducting fibers. The data bus 47 for transferring data from the randomly positioned interconnection point 48 for the sensors to Personal Status Monitors 1 and 2 (PSM 1 and PSM 2) is also shown. The presently preferred PSM is a custom built PSM manufactured by the Sarcos Research Corporation of Salt Lake City, Utah.

The presently preferred PSM is a light weight device that is preferably located at the hip area of the user, i.e. at the bottom of the garment and at an end point of the data buses. The information obtained by the PSM is transmitted to the remote control center, e.g., the medical personnel in the case of military application, by Broadband-Code Division Multiplexing. The transmitter can be attached to the PSM or can be located externally on the outer garment of the user and coupled to the PSM using wire conductors.

Not expressly shown in FIG. 15, but to be included in the elastic board, are modular arrangements and connections for providing power to the electrical conducting material component and for providing a light source for the penetration detection component. The fabric in one form can be made with the sensing component(s) but without inclusion of such power and light sources, or the transmitters 52 and receivers 54 illustrated, expecting such to be separately provided and subsequently connected to the fabric.

E. Operation of the Fabric With Integrated Information Infrastructure

The operation of our above-described fabric having an integrated information infrastructure to illustrate its penetration alert and vital signs monitoring capabilities is now discussed.

Penetration Alert:

1. Precisely timed pulses are sent through the POF integrated into the garment.

2. If there is no rupture of the POF, the signal pulses are received by a transceiver and an "acknowledgement" is sent to the PSM Unit indicating that there is no penetration.

3. If the optical fibers are ruptured at any point due to penetration, the signal pulses bounce back to the first transmitter from the point of impact, i.e., the rupture point. The time elapsed between the transmission and acknowledgement of the signal pulse indicates the length over which the signal has traveled until it reached the rupture point, thus identifying the exact point of penetration. The location of the actual penetration in the POF can be determined by an Optical Time Domain Reflectometer after the penetration is initially detected.

4. The PSM unit transmits a penetration alert via a transmitter specifying the location of the penetration.

Physical Signs Monitoring:

1. The signals from the sensors are sent to the PSM Unit or to a monitoring unit through the electrical conducting component (ECC) of the fabric.

2. If the signals from the sensors are within the normal range and if the PSM Unit has not received a penetration alert, the vital sign readings are recorded by the PSM Unit for later processing. Alternatively, the vital signs data may be transmitted continuously to remote monitoring units.

3. However, if the readings deviate from the normal, or if the PSM Unit has received a penetration alert, the vital sign readings are transmitted using the transmitter.

Thus, the fabric of our present invention is easy to deploy and meets all the functional requirements for monitoring vital signs and/or penetration.

Although the preceding direction has been geared toward military applications the presently described and fabric having an integrated information infrastructure can be adapted to may other applications. For instance, in medical applications the fabric can be utilized by doctors to either continuously or intermittently monitor desired vital signs of patients who are at remote locations. Further, persons who have known disorders can wear the garment and be under constant monitoring of their physical condition by medical personnel. These could include, but are not limited to, monitoring and treatment of: individuals including those in post-operative recovery (e.g., heart surgery); of geriatric patients, especially those in remote areas where the doctor-patient ratio is very small compared to urban areas; of mentally ill patients for a better understanding of diseases such as chronic depression; of children susceptible to SIDS (sudden infant death syndrome); and individual prone to allergic reactions (e.g., anaphylaxis reaction from bee stings).

Just as the home security industry is a big business that monitors and protects homes, our fabric having an integrated information infrastructure has the potential to spawn a new industry for the reliable and effective monitoring of patients at home and thereby transform home healthcare delivery.

Additional applications can include police, fire fighting, mining and other public safety activities where it is desirable to maintain constant updates of information on the physical condition and location of personnel. By combining the physical sensors with GPS (Global Positioning System) the control center can monitor firefighter or police officers' location and physical signals at all times, thereby increasing the safety and ability of these personnel to operate in remote and/or hazardous conditions. Furthermore, the vital signs of drivers (auto, truck, etc.) wearing the fabric garment of our present invention can be monitored continuously and an alarm triggered if the driver becomes drowsy, thereby avoiding accidents.

Our fabric/garment can be used for monitoring astronauts in space in an unobtrusive matter and thereby enhance the knowledge to be gained from medical experiments in space that will lead to new discoveries and the advancement of the understanding of space.

It can be used by athletes to monitor their vital signs and hence their performance. In team sports, the coach can track the vital signs and the performance of the player on the field and make desired changes in the players on the field depending on the condition of the player.

It can also be used in various other settings (e.g., prisons, shops, high security areas, mountaineering/hiking expeditions, etc.) to monitor and track the movement of individuals and their vital signs.

Further, the fabric/garment can also transmit signals that are received by receivers coupled to the data buses or the PSM. These signals can include video, positional signals, information on other members of a group, etc. The information can be transmitted utilizing B-CDMA or other communication protocols. For instance, the received signals can, be voice signals sent through the garment to an ear piece worn by the user. Video data can be supplied to a monitor that is coupled to garment or flat screen display that is attached to the garment. The fabric/garment can utilize separate buses for transmitting and receiving signals if a certain bandwidth is needed for the received signals.

The advantages of incorporating the receive and transmit functions into the single garment include reduction in the amount of equipment the user must manage. For example, a firefighter's microphone and radio can simultaneously communicate using one garment. This allows for a reduction in the number of pieces of equipment that meet to utilized, maintained and tracked. Other advantages include a lighter overall weight carried by the user since no external equipment with its associated casing is utilized.

In addition to transmitting the data of the wearer, the sensors can also act as receivers of external signals (e.g., from the PSM) through the databus in the fabric/garment. This feature can be used to modify the sensitivity of the sensors as needed. For example, the sensitivity of the microphone in the fabric/garment can be changed remotely through the databus.

The fabric/garment allows a new way to customize information processing devices to "fit" the wearer by selecting and plugging in (or removing) chips/sensors from the garment, thus creating a wearable information infrastructure. This will lead to human networks of mobile information processors that interact with each other. For example, the fabric/garment can be connected to the Internet and the wearer can search for information (e.g., on the world wide web), download information or upload information from the fabric/garment to the web, even when the wearer is mobile.

The fabric/garment can also be used to track valuable objects and hazardous substances (e.g., radioactive materials) whose movements must be monitored. For instance, it can be used by banks to wrap money to facilitate their tracking (e.g., in the event of a bank robbery). Monitoring of vital signs of pets is among a myriad of such uses of the fabric.

The fabric/garment can be used to interact with the environment to modifying the surroundings. For instance, depending on the wearer's mood reflected by the vital signs, the ambience (e.g., lighting, music, climate, etc.) can be modified to suit the user's preferences. Thus, the fabric/garment pioneers the class of adaptive and responsive textile structures (ARTS). A related application of the fabric is to interact with Java™ or similarly enabled devices and appliances to carry out specific tasks such as turning on a coffeepot, a microwave, etc.

The vital signs of individuals involved in mission-critical or hazardous operations can be continuously monitored and appropriate action taken. For example, individuals operating mass transportation and/or cargo vehicles can be monitored on a regular basis to prevent or identifying the causes for major disasters (e.g., plane crashes) brought on by the physical impairment of the human operator. Likewise, the vital signs of scuba divers can be reliably monitored from the surface and they can be asked to take appropriate actions (e.g., return to the surface) to prevent injuries and fatalities.

While the invention has been disclosed in its preferred forms, it will be apparent to those skilled in the art that many modifications, additions, and deletions can be made therein without departing from the spirit and scope of the invention and its equivalent as set forth in the following claims.

What is claimed is:

1. A fabric comprising:
    a comfort component serving as the base of the fabric; and
    an information infrastructure component integrated within said comfort component to form the fabric, the information infrastructure component being selected from the group consisting of, individually or in any combination, a penetration detection component and an electrical conductive component, said electrical conductive component comprising one or more individually insulated conductive fibers.

2. A fabric as defined in claim 1, wherein the comfort component includes a yarn selected from the group consisting of fibers of cotton, cotton/polyester blends, microdenier polyester/cotton blends, and polypropylene, and combinations thereof.

3. A fabric as defined in claim 1, wherein the information infrastructure component has attached to it a sensor, a processor or a wireless transmission device, either individually or in combination.

4. A fabric as defined in claim 1, wherein the penetration detection component is selected from the group consisting of silica-based optical fibers, plastic optical fibers, and silicone rubber optical fibers, and combinations thereof.

5. A fabric as defined in claim 1, wherein the electrical conductive component is selected from the group consisting of intrinsically conducting polymers, doped fibers, and metallic fibers, and combinations thereof.

6. A fabric as defined in claim 1, wherein the comfort component is selected from the group consisting of tubular woven and knitted fabric and two-dimensional woven and knitted fabrics.

7. A fabric as defined in claim 1, further comprising a form-fitting component.

8. A fabric as defined in claim 7, wherein the form fitting component is SPANDEX yarn.

9. A fabric as defined in claim 4, wherein the penetration detection component is a sheathed optical fiber having a core diameter of from 225 to 255 microns and a sheath diameter equal to the core diameter plus 0.5 to 1.0 mm.

10. A fabric as defined in claim 9, wherein the penetration sensing component has a bending radius of at least 9 mm.

11. A fabric as defined in claim 1, wherein said information infrastructure component further comprises means for monitoring a physical aspect of a wearer of the fabric selected from the group consisting of heart rate, EKG, pulse rate, temperature, respiration rate, allergic reactions, and voice, and combinations thereof.

12. A fabric as defined in claim 1, wherein said fabric is fashioned into a garment.

13. A fabric comprising:
   a comfort component serving as a base of the fabric; and plurality of signal transmission paths integrated within said comfort component to form the fabric, wherein the plurality of signal transmission paths include either a penetration detection component or an electrical conductive component or both, said electrical conductive component comprising one or more individually insulated conductive fibers.

14. A fabric as defined in claim 13 wherein said plurality of signal transmission paths are woven into said comfort component.

15. A fabric as defined in claim 13, wherein said plurality of signal transmission paths are knitted into said comfort component.

16. A fabric as defined in claim 13 further comprising at least one sensor coupled with the at least one signal transmission path.

17. A fabric as defined in claim 16 wherein said at least one sensor comprises a fabric penetration sensor.

18. A fabric as defined in claim 16 wherein said at least one sensor comprises a sensor that monitors a physical condition of a wearer of the fabric.

19. A fabric as defined in claim 13 further comprising a form fitting component.

20. A fabric as defined in claim 19, wherein the form fitting component is SPANDEX yarn.

21. A fabric as defined in claim 13 which can be used as a wearable, mobile and flexible information infrastructure and personal information processor operating in a stand-alone or networked mode.

22. A fabric as defined in claim 13, wherein the comfort component includes a yarn selected from the group consisting of fibers of cotton, cotton/polyester blends, microdenier polyester/cotton blends, and polypropylene, and combinations thereof.

23. A fabric as defined in claim 13, wherein the plurality of signal transmission paths have attached to at least one of said paths a sensor, a processor or a wireless transmission device, either individually or in combination.

24. A fabric as defined in claim 13, wherein the penetration detection component is selected from the group consisting of silica-based optical fibers, plastic optical fibers, and silicone rubber optical fibers, and combinations thereof.

25. A fabric as defined in claim 13, wherein the electrical conductive component is selected from the group consisting of intrinsically conducting polymers, doped fibers, and metallic fibers, and combinations thereof.

26. A fabric as defined in claim 13, wherein the comfort component is selected from the group consisting of tubular woven and knitted fabrics and two dimensional woven and knitted fabrics.

27. A fabric as defined in claim 24, wherein the penetration detection component is a sheathed optical fiber having a core diameter of from 225 to 255 microns and a sheath diameter equal to the core diameter plus 0.5 to 1.0 mm.

28. A fabric as defined in claim 27, wherein the penetration detection component has a bending radious of at least 9 mm.

29. A fabric as defined in claim 13, wherein said fabric is fashioned into a garment.

30. A fabric as defined in claim 1, wherein the information infrastructure component has attached to it a sensor, processor or a wireless transmission device, either individually or in combination, and is selected from the group consisting of, either alone or in combination,
   a. a penetration detection component selected from the group consisting of silica-based optical fibers, plastic optical fibers, and silicone rubber optical fibers, and combinations thereof; and
   b. an electrical conductive component selected from the group consisting of intrinsically conducting polymers, doped fibers, and metallic fibers, and combinations thereof.

31. A fabric as defined in claim 13, wherein the plurality of signal transmission paths have attached to at least one of said paths a sensor, a processor or a wireless transmission device, either individually or in combination, and wherein the signal transmission paths are selected from the group consisting of, either alone or in combination,
   a. a penetration detection component selected from the group consisting of silica-based optical fibers, plastic optical fibers, and silicone rubber optical fibers, and combinations thereof; and
   b. an electrical component selected from the group consisting of intrinsically conducting polymers, doped fibers, and metallic fibers, and combinations thereof.

* * * * *